United States Patent [19]

Miremadi

[11] Patent Number: 5,987,964
[45] Date of Patent: Nov. 23, 1999

[54] APPARATUS AND METHOD FOR DETECTING GAS AND VAPOR

[75] Inventor: Bijan K. Miremadi, Coquitlam, Canada

[73] Assignee: Simon Fraser University, Burnaby, Canada

[21] Appl. No.: 09/049,086

[22] Filed: Mar. 27, 1998

Related U.S. Application Data

[60] Provisional application No. 60/041,653, Mar. 27, 1997.

[51] Int. Cl.$^6$ .................................................. G01N 27/12
[52] U.S. Cl. .......................................... 73/31.05; 73/23.2
[58] Field of Search ................................... 73/31.05, 23.2

[56] References Cited

U.S. PATENT DOCUMENTS

| | | |
|---|---|---|
| 4,327,054 | 4/1982 | Yasuda et al. . |
| 4,377,944 | 3/1983 | Hishii et al. . |
| 4,457,161 | 7/1984 | Iwanaga et al. ................... 73/31.05 X |
| 4,542,640 | 9/1985 | Clifford ............................. 73/31.05 X |
| 4,586,143 | 4/1986 | Kaneyasu et al. ................. 73/31.05 X |
| 4,638,443 | 1/1987 | Kaneyasu et al. ................. 73/31.05 X |
| 4,670,405 | 6/1987 | Stetter et al. ........................ 73/23.2 X |
| 4,907,441 | 3/1990 | Shurmer ............................. 73/31.05 X |
| 5,025,653 | 6/1991 | Schuldt .................................... 73/23.2 |
| 5,298,783 | 3/1994 | Wu . |
| 5,305,231 | 4/1994 | Coppler et al. .......................... 364/497 |
| 5,415,760 | 5/1995 | Hitomi et al. . |
| 5,426,934 | 6/1995 | Hunt et al. . |

*Primary Examiner*—Daniel S. Larkin
*Attorney, Agent, or Firm*—Hall, Priddy & Myers

[57] ABSTRACT

A gas detection circuit for use in selectively detecting a predetermined gas has a plurality of gas sensors coupled to a sensor measuring circuit. Each gas sensor has a different response to the predetermined gas at a predetermined concentration. The sensor measuring circuit measures a conditioned state of each gas sensor and transmits the measurements to a cross checking circuit which determines whether the conditioned state of each gas sensor is within a corresponding window of upper and lower limit values thereby indicating the possible presence of the predetermined gas by the corresponding gas sensor. Following the testing of the conditioned state of each gas sensor, the cross checking circuit transmits a signal indicating which of the gas sensors indicates the possible presence of the predetermined gas and if all sensors are within corresponding windows, representing detection of the gas, another signal is transmitted to trigger an alarm or other warning system.

20 Claims, 12 Drawing Sheets

Sensitivity characteristics of the TGS 813

♦ Remarks : Ro: Sensor resistance in air containing 1000ppm of methane
Rs: Sensor resistance at different concentrations of gases.

Sensitivity characteristics of the TGS 822

♦ Remarks : Ro: Sensor resistance in air containing 300ppm of ethanol
Rs: Sensor resistance at different concentrations of gases Sensitivity characteristics of the TGS 812

♦ Remarks : Ro: Sensor resistance in air containing 1000ppm of isobutane
Rs: Sensor resistance at different concentrations of gases Flow chart of routines

|  | Sensor 1 | Sensor 2 | Sensor 3 |
|---|---|---|---|
|  | TGS 813 | TGS 812 | TGS 822 |
| Concentration ppm | Rs k-ohm | Rs k-ohm | Rs k-ohm |
| $H_2$ | | | |
| 0 | 76 | 128 | 60 |
| 25 | 34.5 | 7.7 | 10.2 |
| 50 | 27.2 | 4.6 | 7.1 |
| 100 | 23.2 | 3.4 | 5.7 |
| 250 | 14.3 | 1.7 | 3.1 |
| 500 | 10.4 | 1.1 | 2.1 |
| 800 | 8.1 | 0.85 | 1.6 |
| 1000 | 7.2 | 0.75 | 1.4 |
| 1200 | 6.6 | 0.72 | 1.3 |
| 1500 | 5.9 | 0.62 | 1.1 |
| 1800 | 5.3 | 0.52 | 1 |

Arbitrary selection of the window widths.

Window set for 500 ppm

Unit operates as a HYDROGEN sensor

|  | | | |
|---|---|---|---|
| upper | 24 | 3.2 | 3 |
| lower | 8.2 | 0.5 | 1 |

FIG. 15

|  | Sensor 1 | Sensor 2 | Sensor 3 |
|---|---|---|---|
|  | TGS 813 | TGS 812 | TGS 822 |
| Concentration ppm | Rs k-ohm | Rs k-ohm | Rs k-ohm |
| $CH_4$ | | | |
| 0 | 76 | 128 | 60 |
| 25 | 54.3 | 103.4 | 52.1 |
| 50 | 43.3 | 87.3 | 44.7 |
| 100 | 37.3 | 78.3 | 40.2 |
| 250 | 20.4 | 50.5 | 27.3 |
| 500 | 14.8 | 37.5 | 20.8 |
| 800 | 11.3 | 26.5 | 16.8 |
| 1000 | 9.9 | 25.2 | 15.2 |
| 1200 | 9.2 | 22.6 | 14.1 |
| 1500 | 8.2 | 20.2 | 13.1 |
| 1800 | 7.5 | 18.3 | 12.2 |

Window set for 500 ppm

Unit operates as a METHANE sensor

|  | | | |
|---|---|---|---|
| upper | 24 | 50 | 24 |
| lower | 8.2 | 24 | 8.2 |

FIG. 16

|  | Sensor 1 | Sensor 2 | Sensor 3 |  | Sensor 1 | Sensor 2 | Sensor 3 |
|---|---|---|---|---|---|---|---|
|  | TGS 813 | TGS 812 | TGS 822 |  | TGS 813 | TGS 812 | TGS 822 |
| Concentration ppm | Rs k-ohm | Rs k-ohm | Rs k-ohm | Concentration ppm | Rs k-ohm | Rs k-ohm | Rs k-ohm |
|  | CO | | | | Propane | | |
| 0 | 76 | 128 | 60 | 0 | 76 | 128 | 60 |
| 25 | 65.3 | 42.5 | 25.6 | 25 | 38.9 | 32.6 | 20.1 |
| 50 | 61.5 | 21.6 | 18.5 | 50 | 31.3 | 21.2 | 14.8 |
| 100 | 56.3 | 19.1 | 15.1 | 100 | 27.6 | 16.7 | 12.3 |
| 250 | 43.1 | 8.5 | 8.3 | 250 | 17.3 | 7.6 | 7.5 |
| 500 | 35.8 | 5.7 | 6.1 | 500 | 12.7 | 4.7 | 5.6 |
| 800 | 31.2 | 4.3 | 4.7 | 800 | 10.1 | 3.3 | 4.6 |
| 1000 | 28.7 | 3.6 | 4.1 | 1000 | 8.6 | 2.8 | 4.1 |
| 1200 | 27.2 | 3.3 | 3.7 | 1200 | 7.9 | 2.5 | 3.7 |
| 1500 | 25.6 | 2.9 | 3.4 | 1500 | 7.2 | 2.2 | 3.5 |
| 1800 | 24.3 | 2.7 | 3.1 | 1800 | 6.5 | 2.1 | 3.3 |

Window set for 500 ppm

Unit operates as a CO sensor

| | | | | | | | |
|---|---|---|---|---|---|---|---|
| upper | 43 | 8 | 8 | upper | 24 | 8 | 7 |
| lower | 30 | 4 | 4.5 | lower | 8.2 | 3.6 | 4 |

Window set for 500 ppm

Unit operates as a PROPANE sensor

FIG. 17     FIG. 18

APPARATUS AND METHOD FOR DETECTING GAS AND VAPOR

This application claims the benefit of U.S. Provisional Application No. 60/041,653 filed Mar. 27, 1997.

FIELD

The present invention relates to the field of gas and vapor detection for residential, commercial, and industrial applications. More particularly, the present invention relates to an apparatus and a method for the detection of a predetermined gas and its vapor in the presence or absence of other gases.

BACKGROUND

Gas sensors and gas detection systems are well known in the art. Conventional gas detection systems, however, typically detect the presence or absence of a gas based on information from a single gas sensor. A problem which arises with such conventional systems is that the gas sensor may be sensitive to more than one type of gas molecule. Thus, where the gas detection system is configured to detect a predetermined gas molecule, such as natural gas, methane, carbon dioxide, or carbon monoxide, the presence of other gas molecules to which the sensor is sensitive can result in the false detection of the predetermined gas. Furthermore, where two or more gases to which a gas sensor is sensitive substantially co-exist, it can be difficult to determine the extent to which the predetermined gas is present. For instance, certain industries make use of gas sensors to detect hydrazine. Existing sensors, however, are sensitive to both hydrogen and hydrazine molecules and there is a long-felt need in these industries for a gas detection system capable of distinguishing between these two molecules.

Accordingly, it is an object of the invention to provide an improved apparatus for detecting a predetermined gas which fulfills the above needs in the art. It is a further object of the invention to provide an apparatus for detecting a predetermined gas with two or more gas sensors so as to accurately detect the presence of a predetermined gas. It is yet a further object of this invention to provide a simple, low cost apparatus for detecting a predetermined gas. It is a further object of the invention to provide a gas detection system which is readily applicable for the detection of many different gases and which can be easily configured to detect a selected gas.

SUMMARY OF THE INVENTION

According to the invention, there is provided a gas detection circuit for selectively detecting a predetermined gas. The gas detection circuit, comprises a plurality of gas sensors, a sensor measuring circuit, and a cross checking circuit. Preferably, each gas sensor has a conditioned state different from the other gas sensors in the presence of the predetermined gas at a predetermined concentration. The sensor measuring circuit is coupled to each of the gas sensors and is operative to: (i) measure the conditioned state of each of the gas sensors; and (ii) produce, for each conditioned state measured in (i), an output signal characteristic thereof. The cross checking circuit is coupled to the sensor measuring circuit and is operative to: (i) receive each of the output signals corresponding to the respective gas sensors from the sensor measuring circuit; (ii) determine, for each of the output signals received in from the sensor measuring circuit, if a corresponding one of the gas sensors has indicated a possible presence of the predetermined gas based on the conditioned state of the corresponding gas sensor; and (iii) transmit a detection signal identifying which of the gas sensors has indicated the possible presence of the predetermined gas.

In one embodiment, each gas sensor includes a sensing material in which the electron charge transport is a resistive medium and the conditioned state of each gas sensor as measured by the sensor measuring circuit corresponds to a resistance of the respective resistive medium.

The sensor measuring circuit may measure an upper limit value and a lower limit value for each of the gas sensors, where each pair of upper and lower limit values defines a window within which the possible presence of the predetermined gas is indicated. In this embodiment, the sensor measuring circuit transmits each pair of upper and lower limit values to the cross checking circuit where they are compared with the conditioned state of the corresponding gas sensor to determine if the conditioned state falls within this window of upper and lower limit values.

The gas detection circuit may include a pair of limit resistors for each of the gas sensors with the upper and lower limit values of each gas sensor corresponding to a resistance of one of the limit resistors.

In another embodiment, the gas detection circuit includes a capacitor coupled to the limit resistors and sensor resistors. In this embodiment, the resistances of the sensor resistors and the limit resistors may be measured indirectly by measuring, for each such resistor, the time required to charge the capacitor to a predetermined charge by applying a voltage through the respective resistor.

The gas detection circuit may also include a heater so as to maintain a sensor resistive compound in each of the gas sensors at a temperature above an ambient temperature of air.

In a preferable embodiment, the gas detection circuit includes at least three gas sensors, each having a different response to the predetermined gas at a predetermined concentration, thereby improving the gas detection circuit's selectively towards the predetermined gas over other gases.

The gas detection circuit may be configured to detect the presence of one of various gases and their vapors, including carbon dioxide, carbon monoxide, methane, ethanol, propane, isobutane, hydrogen, hydrazine, benzene, and ammonia.

In another aspect of the present invention, there is provided a method of selectively detecting a predetermined gas with a plurality of gas sensors, each gas sensor having a response different from that of the other gas sensors in the presence of a predetermined gas at a predetermined concentration. In this method, for each of the gas sensors a value is measured corresponding to a state of the respective gas sensor. Each value measured is then compared with upper and lower limit values corresponding to the same gas sensor as the measured value. If the measured value is within the window defined by the upper and lower limit value, the gas sensor to which the measured value corresponds has indicated a possible presence of the predetermined gas. A signal is then transmitted identifying which of the gas sensors indicates the possible presence of the predetermined gas.

In one embodiment, an LED display is triggered for each gas sensor which is determined to have indicated the possible presence of the predetermined gas.

BRIEF DESCRIPTION OF THE DRAWINGS

The novel features believed characteristic of the invention are set forth in the appended claims. The invention itself, however, as well as other features and advantages thereof, will be best understood by reference to the detailed description which follows, read in conjunction with the accompanying drawings, wherein:

FIG. 15 is a table illustrating the use of gas sensors TGS-813, TGS-812, and TGS-822 to selectively detect the presence of hydrogen in accordance with the present invention;

FIG. 16 is a table illustrating the use of gas sensors TGS-813, TGS-812, and TGS-822 to selectively detect the presence of methane in accordance with the present invention;

FIG. 17 is a table illustrating the use of gas sensors TGS-813, TGS-812, and TGS-822 to selectively detect the presence of carbon monoxide in accordance with the present invention; and FIG. 18 is a table illustrating the use of gas sensors TGS-813, TGS-812, and TGS-822 to selectively detect the presence of propane in accordance with the present invention.

DETAILED DESCRIPTION

This application claims the benefit of U.S. Provisional Application No. 60/041,653 filed Mar. 27, 1997, the whole of which is incorporated herein by reference.

Figure 1:
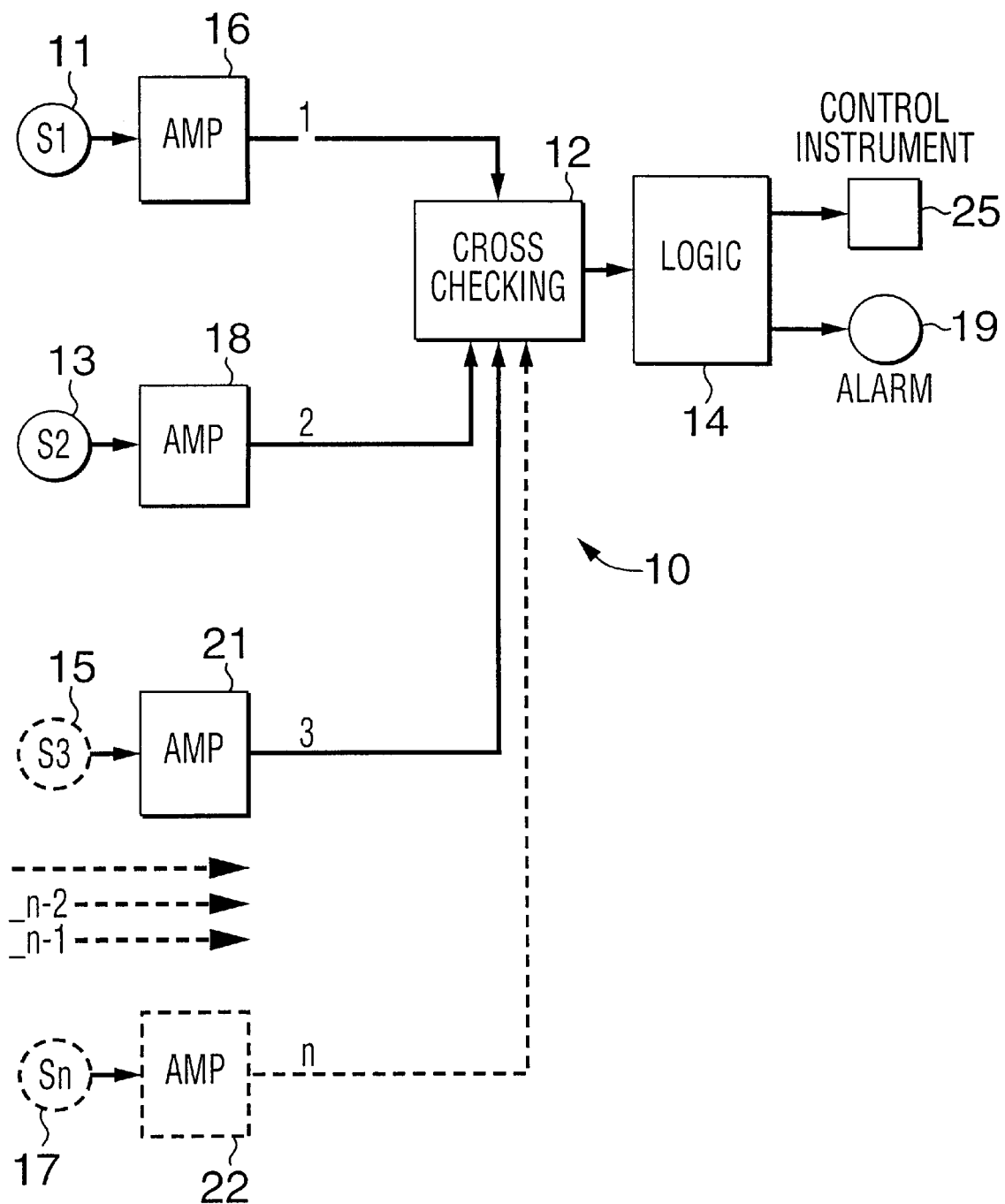
FIG. 1 is a block diagram of one embodiment of a gas detection system in accordance with the present invention.
Figure 2:
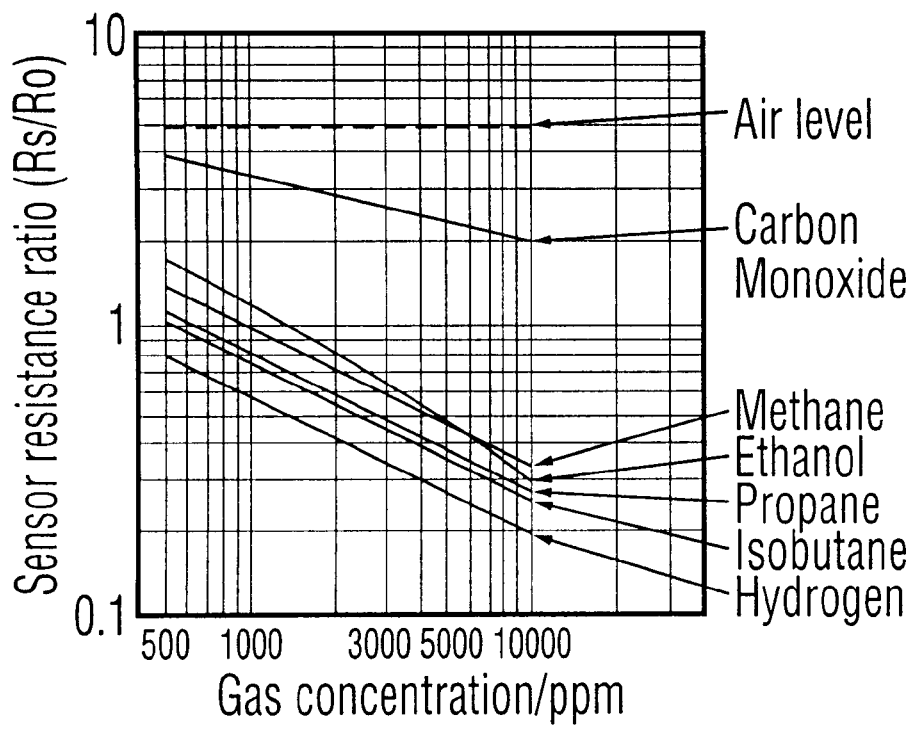
FIG. 2 is a chart showing the ratio of resistance (R/Ro) vs. concentration for the Figaro gas sensor model TGS-813.
Figure 3:
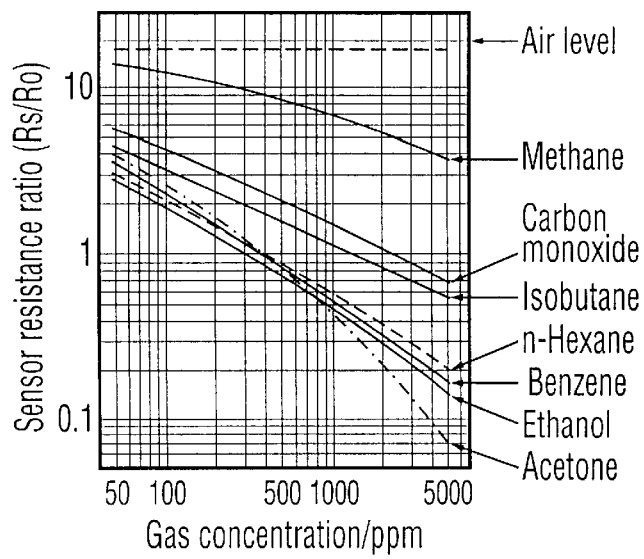
FIG. 3 is a chart showing the ratio of resistance (R/Ro) vs. concentration for the Figaro gas sensor model TGS-822.
Figure 4:
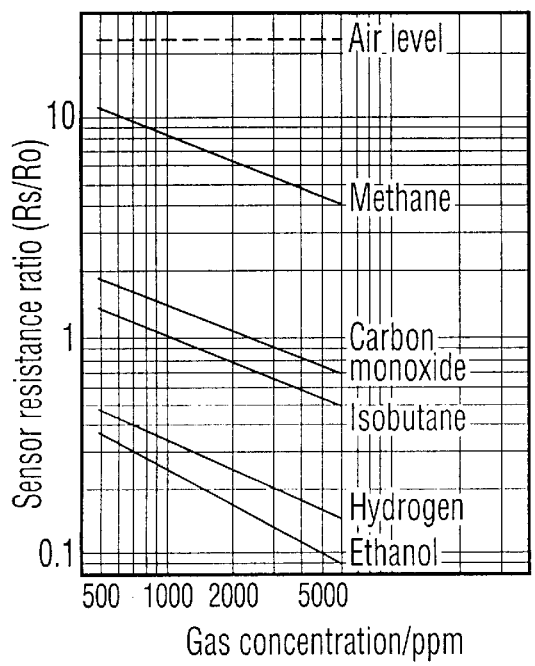
FIG. 4 is a chart showing the ratio of resistance (R/Ro) vs. concentration for the Figaro gas sensor model TGS-812.

Referring to FIG. 1, gas detection system 10 employs n gas sensors 11, 13, 15, and 17 each of which has a resistor having a different sensitivity to a particular gas. FIGS. 2, 3, and 4 are graphs showing, by way of example, the sensitivities of three gas sensors to particular gases, with sensitivities shown by the relationship between the concentration of a particular gas in air and sensor resistance changes given by a ratio (Rs/Ro) of the resistance of the sensor resistor (Rs) at different concentrations of gases divided by the resistance of that sensor resistor in air containing a particular concentration of a particular gas (Ro). The curves shown are on a logarithmic scale and correspond to a given ambient temperature. Temperature is set for each sensor by a heater whose current is electronically controlled. FIG. 2 shows the curves for a Figaro model TGS-813 sensor wherein Ro represents sensor resistance in air containing 1000 ppm of methane. FIG. 3 shows the curves for a Figaro model TGS-822 sensor wherein Ro represents sensor resistance in air containing 300 ppm of Ethanol. FIG. 4 shows the curves for a Figaro model TGS-812 sensor wherein Ro represents sensor resistance in air containing 1000 ppm Isobutane. Each of the sensors corresponding to FIGS. 2, 3, and 4 is commercially available from Figaro Corporation, although it will be appreciated that the use of other commercially available gas sensors are also contemplated within the scope of the present invention.

In selecting different gas sensors, it should be noted that the difference in sensitivities between gas sensors to a particular gas should be sufficiently great so as to distinguish between the resistances produced by the different gas sensors in the presence of the particular gas.

Referring to FIG. 1, the output of the circuit containing each sensor 11, 13, 15, and 17 is a time value for charging a capacitor through the respective sensor resistor. These outputs are each coupled to respective amplifiers 16, 18, 21, and 22 all of which amplify and couple to a cross-checking circuit 12 whose function is to evaluate the various signals as will be discussed in more detail below. The output of the cross-checking circuit 12 is coupled to a logic circuit 14.

Detection of a particular gas by a particular gas sensor is determined in cross checking circuit 12. By using more than one gas sensor with a resistance in a given gas differing significantly from that of another gas sensor in the same gas of the same concentration, one can distinguish from various different gases which might produce the same resistance value amongst the different gas sensors, but at different concentrations of the gas in air. Using at least two different gas sensors allows for this distinction, although there are cases where there may be little difference between the resistance values of two different sensors. Using three sensors with good separation between the resistance values for the desired gas to be measured improves the ability of the gas detection system 10 to selectively detect the desired gas. The gas detection system 10 can be made even more selective to a desired gas through the use of additional gas sensors, each having a different sensitivity to the desired gas at a particular concentration.

Figure 5:
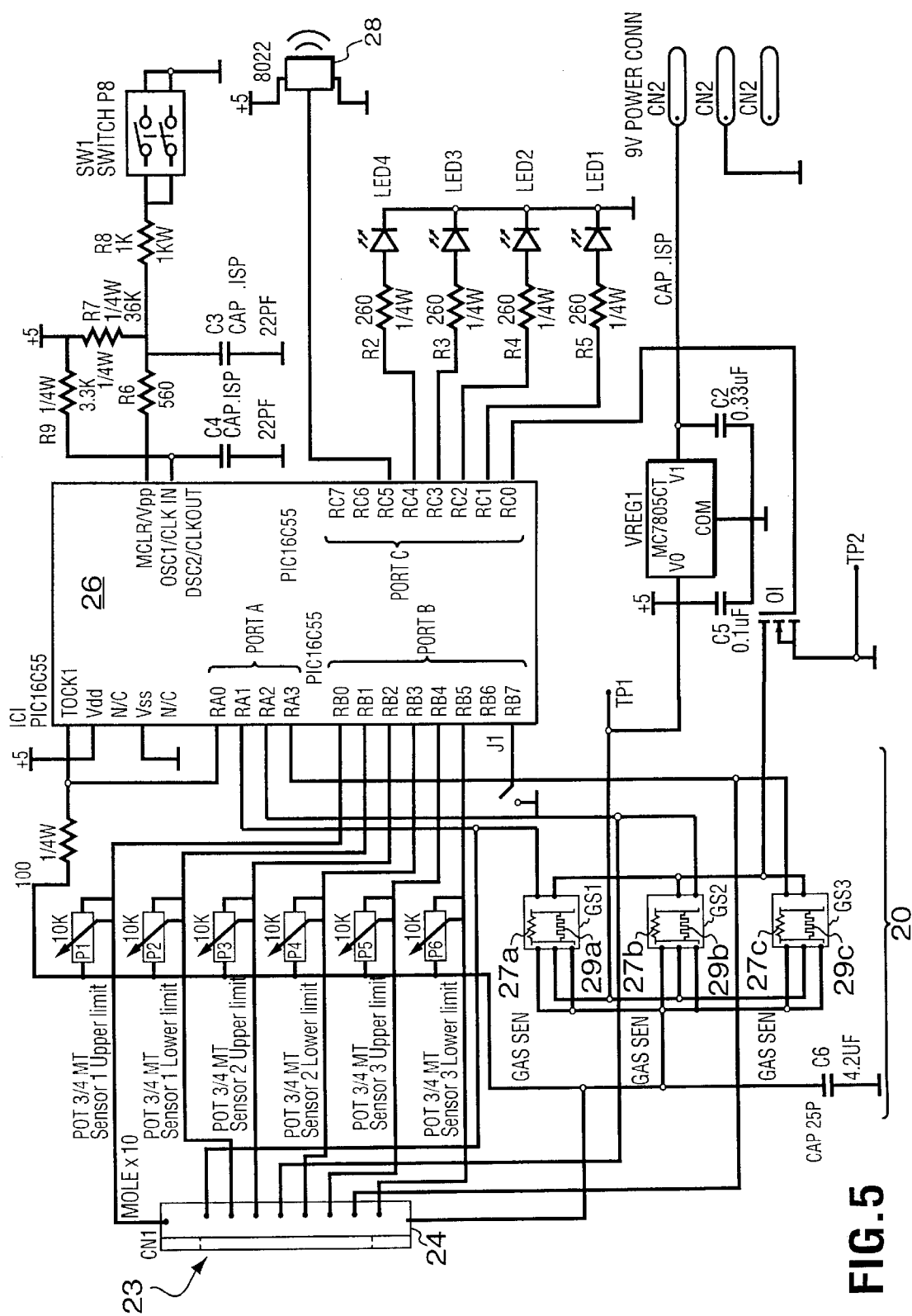
FIG. 5 is a circuit diagram for a gas detection circuit in accordance with the present invention.

As depicted in FIG. 5, variable resistors P1 to P6 are used to set upper and lower resistance values around the particular gas sensor resistor (27a, 27b, or 27c) for each of the gas sensors (GS1 to GSn, where in the illustrated case n=3) defining a respective window. Resistance values for each sensor resistor are measured by a sensor measuring circuit (within microprocessor 26) and compared with their respective windows by cross-checking circuit 12, following which an output signal V is transmitted by logic circuit 14. Output signal V may be used to trigger an alarm 19, to activate an electrical relay, or to control an LED display by means of control circuit 25. In the present case, a green LED is lit for each gas sensor indicating the possible presence of a particular gas and alarm 19 is activated when all sensors indicate the possible presence of a particular gas.

Referring in more detail to FIG. 5, there is shown a circuit diagram 23 for a preferred embodiment of the gas detection unit contemplated in the present invention. Circuit 23 includes connector 24, the pins of which connect directly to pins of microprocessor 26. The pins of connector 24 are also coupled to variable resistors P1, P2, P3, P4, P5, and P6. Circuit 23 further includes gas sensors GS1, GS2, and GS3 which are connected to connector 24 and to pins RA1, RA2, and RA3 of port A of microprocessor 26. Gas sensors GS1, GS2, and GS3 includes a respective sensor resistor 27a, 27b, and 27c and a respective sensor heater wire 29a, 29b, and 29c. In the embodiment shown, sensor resistors 27a, 27b, and 27c each have a different sensitivity to a particular gas. Sensor heater wires 29a, 29b, and 29c are employed to maintain the sensor resistive medium of the corresponding gas sensors GS1, GS2, and GS3 above an ambient temperature.

In circuit 23, resistor pairs P1–P2,P3–P4, and P5–P6 are used as limit resistors to establish the upper and lower resistance limit values or window for each corresponding sensor. Connector 24 and variable resistors P1 to P6 are coupled to the pins of port B of microprocessor 26, namely to pins RB0 to RB5.

The cross checking functions previously discussed are performed in microprocessor 26, and are discussed in further detail below. Microprocessor 26 is coupled at pins RC1 to RC4 to LED1 to LED4, respectively. LED1 to LED3 provide visual display of which sensors GS1, GS2, and GS3 have indicated the possible presence of the particular gas. There is also included an alarm output RC5 coupled to buzzer 28 operative to produce an audible signal indicating that all sensors are in their respective resistance windows and have indicated the possible presence of the predetermined gas. In the embodiment shown, LED4 provides a visual alarm when all sensors are within their resistance windows, in conjunction with the audio alarm of buzzer 28. Pin RB7 of port B is connected to a jumper, J1, which, in a first position, is closed to disable microprocessor 26 as discussed below.

Figure 6:
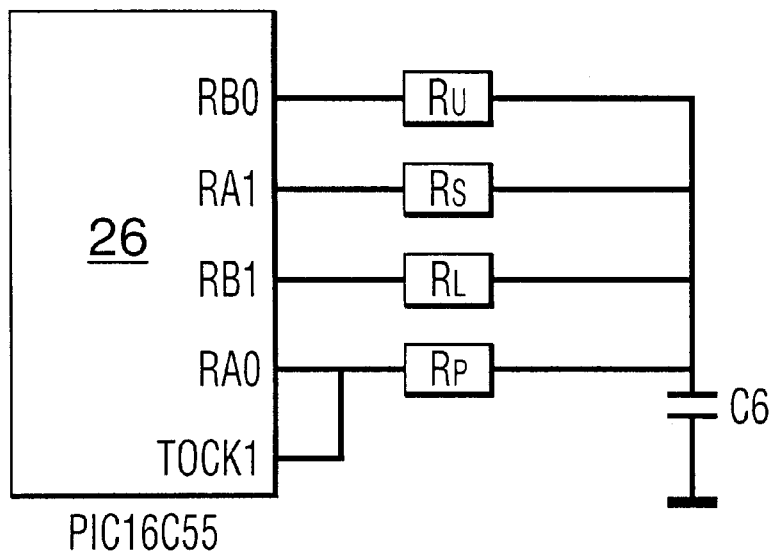
FIG. 6 is a block diagram illustrating the use of a microprocessor to measure the time required to charge capacitor C6 with a reference voltage applied to various resistors.

In operation, the measurement of resistance for each gas sensor GS1, GS2, and GS3 and for resistors P1 to P6 is achieved in the embodiment illustrated in FIG. 5 by employing a capacitive charging circuit 20 to convert resistance to time using a microcontroller. As illustrated in FIG. 6 with respect to gas sensor GS1, a reference voltage is first applied to an upper limit resistor Ru (by way of example, P1 in circuit 23) having a measured resistance and capacitor C6 is charged until a predetermined threshold on an input to the charging circuit trips. The time taken to reach this threshold is measured and stored by microprocessor 26 and is a measure of the resistance in upper limit resistor Ru. Capacitor C6 is then discharged wherein a small resistor Rp (i.e. 100 ohm resistor R1 in circuit 23) may be used to limit peak current while discharging. After capacitor C6 is discharged, the reference voltage is applied to a lower limit resistor R1 (P2 in circuit 23) and then to a sensor resistor Rs (sensor resistor 27a in circuit 23) to determine the lower resistance limit and sensor resistance, respectively. The time to measure each value on TOCK1 is then compared by microprocessor 26 and the results stored.

Figure 7:
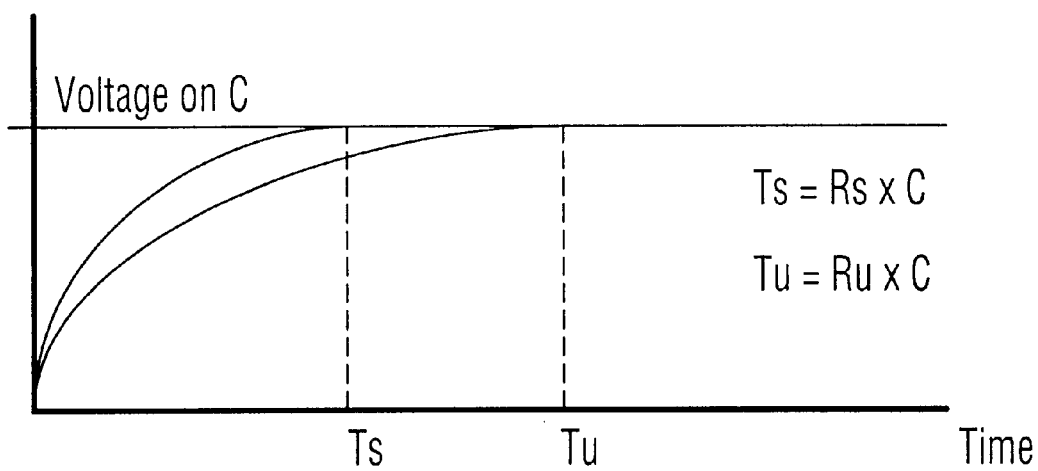
FIG. 7 is a graph illustrating the measurement of the times required to charge capacitor C with a reference voltage applied to resistor Rs and Ru respectively.

Referring to FIGS. 5, 6, and 7, it will be noted that the value of C6 is selected based on the number of bits of resolution required. While measurement time and coding requirements can be substantially reduced for an 8 bit operation, in order to improve accuracy it is preferable that a high bit resolution, such as a 16 bit resolution, is selected. The value of C6 is calculated as follows:

TABLE 1

$$C = \frac{-T}{R_M * \ln(1 - Vt/Vr)}$$

Vr = Reference voltage
Vt = Threshold voltage of the microcontroller
$R_M$ = Maximum measured resistance
T = Time to perform the resolution required By way of example, in one embodiment having a 16 bit resolution, T is 393.2 ms, Vr is 5 V, Vt is 3 V,) and RM is 200 kilo Ohm, so that C is 2.1 uF. In order to avoid overcounting during measurements, C6 should be smaller than the value calculated for C.

Figure 8:
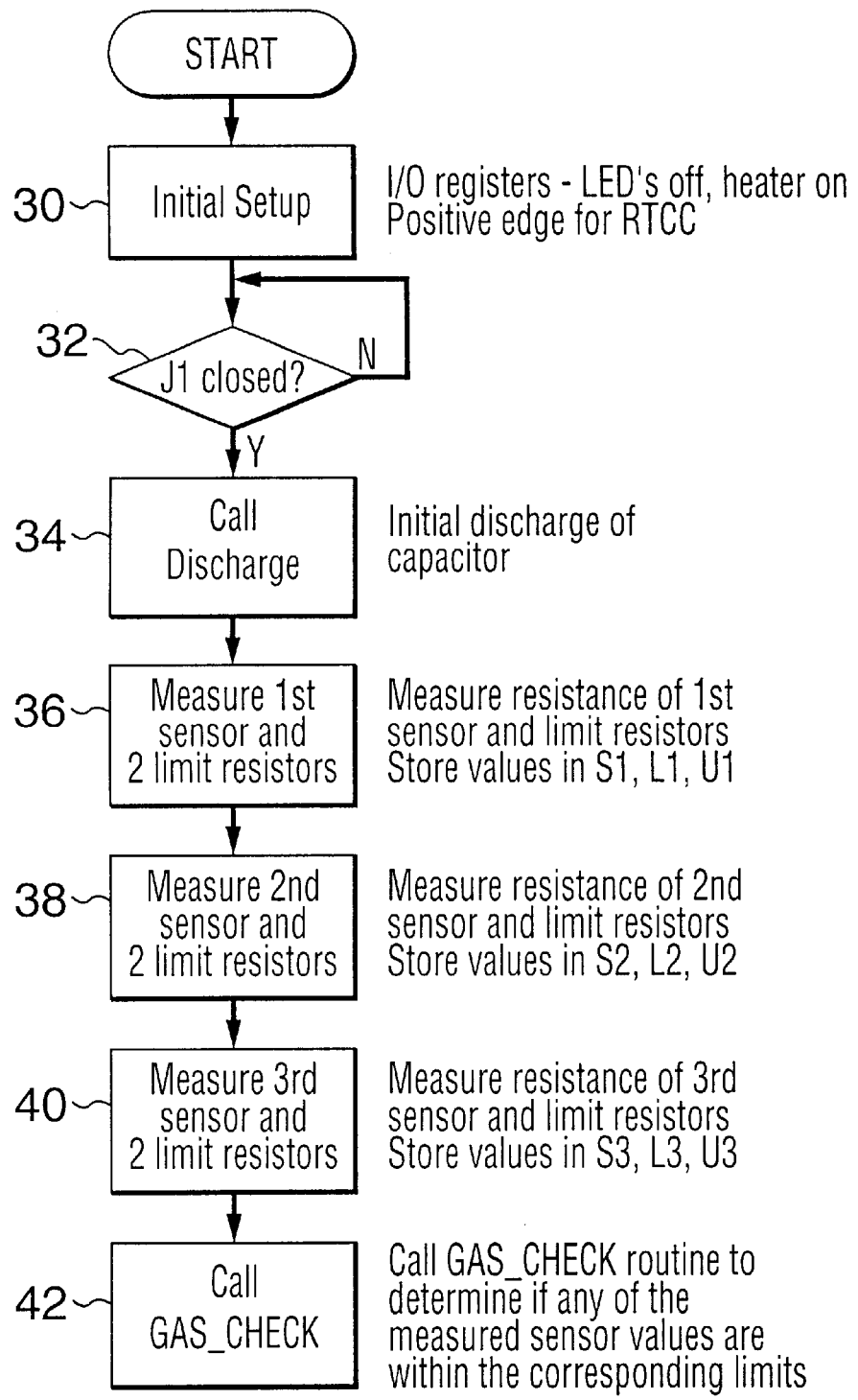
FIG. 8 is a flow chart illustrating one embodiment of the method of detecting a predetermined gas in accordance with the present invention.

Referring to FIG. 8, a flow diagram illustrates a preferred manner of employing circuit 23. Initialization of circuit 23 occurs at step 30. A jumper J1 is connected to RB7 in circuit 23 and is closed at step 32 to disable operation of microprocessor 26 so as to permit accurate measurement of the sensor resistance and the upper and lower limit variable resistors for each corresponding gas sensor GS1, GS2, and GS3. As discussed earlier, in the embodiment illustrated in FIG. 5, microprocessor 26 measures and stores the time required to charge capacitor C6 to a predetermined threshold with a reference voltage applied through each of sensor resistors 27a, 27b, and 27c and limit resistors P1 to P6. Thus, in circuit 23 resistance is measured indirectly by measuring the time required to charge capacitor C6 to a predetermined threshold. However, it will be appreciated that one may alternatively measure resistance directly as is also contemplated within the present invention.

Figure 10:
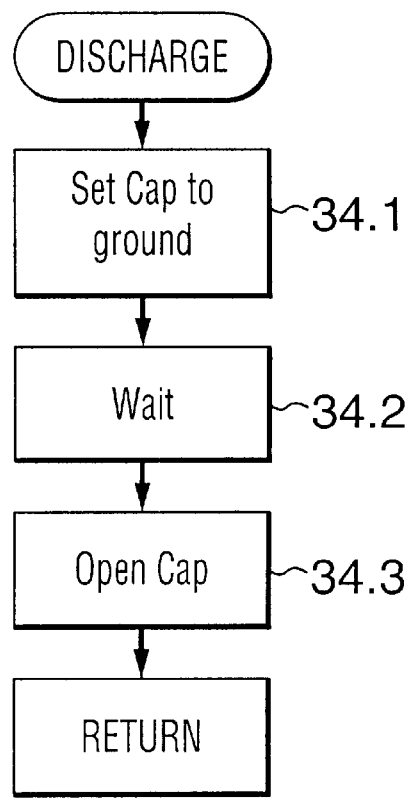
FIG. 10 is a flow chart illustrating one embodiment of the steps for discharging capacitor C6.
Figure 9:
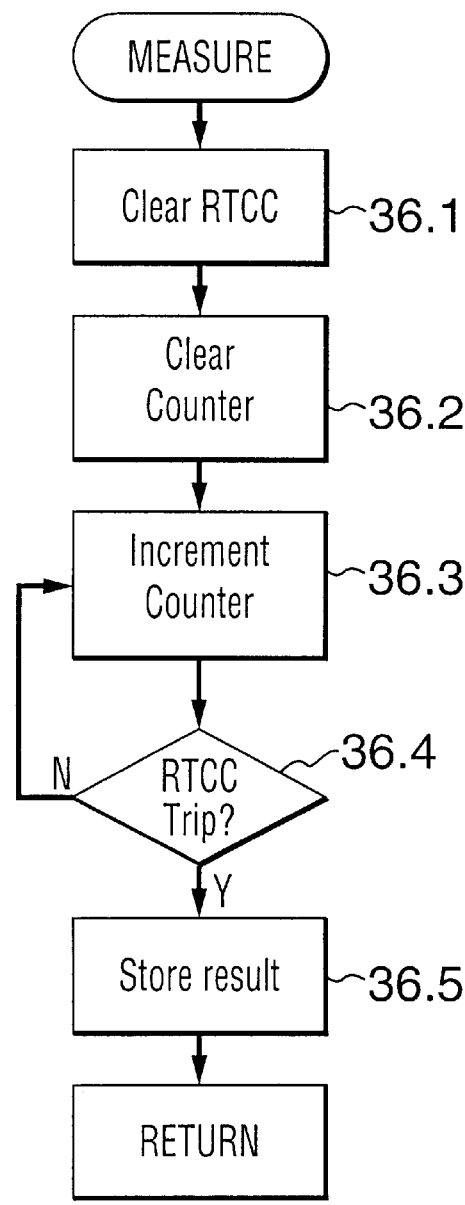
FIG. 9 is a flow chart illustrating one embodiment of the steps for measuring the time required to charge capacitor C6 with a reference voltage.

When J1 is closed at step 32, capacitor C6 in circuit 23 is discharged (as exemplified in FIG. 10) through resistor R1 and the input pins TOCK1 and RA0 of microprocessor 26 at step 34. Referring to FIG. 10, this discharge involves closing J1 to disable the microprocessor 26 and initiating discharge of C6 through R1 and U.S. patent application Ser. No. 09/049,086 input pins TOCK1 and RA0 at step 34.1. After waiting at step 34.2 for C6 to discharge, the jumper J1 is opened and the system returns to step 36. The time equivalent of the resistance of each sensor resistor 27a, 27b, and 27c and the corresponding limit resistors are measured and stored. For the three sensor embodiments in FIG. 5, the time required to charge capacitor C6 with a reference voltage applied through sensor resistor 27a and corresponding limit resistors (P1 and P2) is measured and stored in step 36. Thus, in the embodiment illustrated, the measured time to charge capacitor C6 through sensor resistor 27a is stored in variable S1. The measured time values corresponding to the upper and lower resistance limits P1 and P2 are stored in variables U1 and L1, respectively. Similarly, the time required to charge capacitor C6 by applying a reference voltage through sensor resistor 27b and its limit resistors (P3 and P4) is measured in step 38 by microprocessor 26 and the time values stored in S2, U2, and L2, respectively. The time values corresponding to sensor resistor 27c and its limit resistors (P5 and P6) are measured in step 40 and their values are then stored in S3, U3, and L3, respectively. The measurement and storage of the above time values is further illustrated in FIG. 9. In FIG. 9 the first step 36.1 in the measurement is to clear the RTCC counter that records the digital value of the voltage across capacitor C6 and in step 36.2 to clear the counter that counts clock pulses. The first measurement is the time to charge the first sensor resistor. The counters are both activated and begin counting. After each count the value in the RTCC counter is compared at step 36.4 with the voltage corresponding to a threshold value in the U.S. patent application Ser. No. 09/049,086 microprocessor 26 until that value has been reached. If not yet reached, the system returns to step 36.3 where the RTCC counter is incremented and the threshold test at step 36.4 is repeated. Once the threshold value is reached the value of the time counter, S1, is stored in memory and the system returns to the start where it measures first the upper and then the lower limit resistor charging times U1 and L1, respectively, and also stores those values. The system returns to step 38.

Once the time values corresponding to the resistance for each sensor resistor 27a, 27b, and 27c and the corresponding limit resistors have been measured and the values stored, subroutine 42 is called within microprocessor 26 to determine if any of the measured time values for sensor resistors 27a, 27b, and 27c are within the time values measured for their corresponding upper and lower limit resistors.

Figure 11:
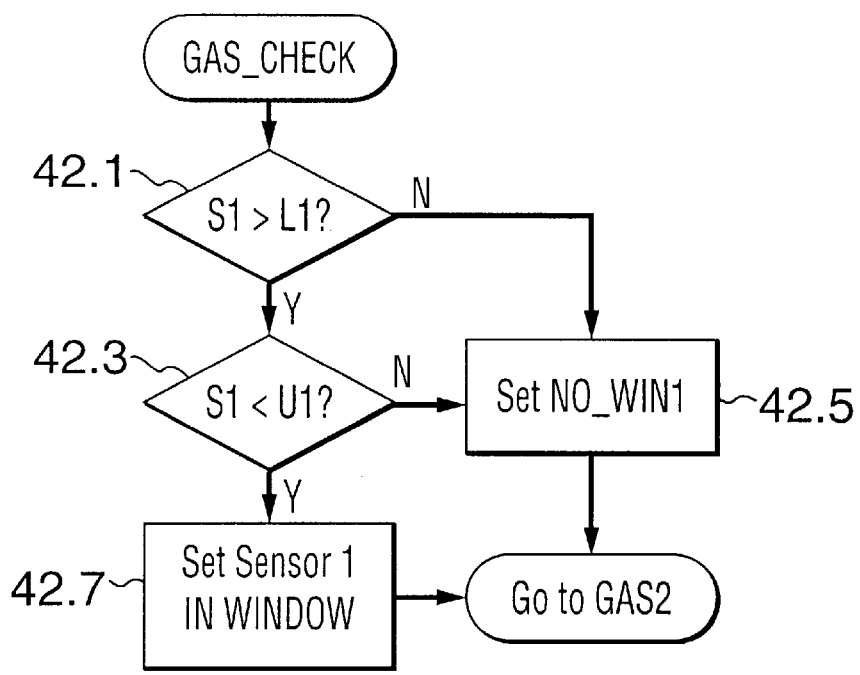
FIG. 11 is a flow chart illustrating one embodiment of the steps for determining if the sensor resistance for sensor resistor 27a of FIG. 5 is within a window of upper and lower limit values in accordance with the present invention.

Referring to FIG. 11, upon execution of subroutine 42 the time value S1 measured for sensor resistor 27a is compared with the lower (L1) and upper (U1) time limits measured for corresponding upper and lower limit resistors P1 and P2 to determine if the possible presence of the particular gas is indicated. In step 42.1, the time value S1 for sensor resistor 27a is compared with lower limit L1. If S1 is less than or equal to L1, the flag NO_WIN1 is set at step 42.5 indicating that the sensor resistance for sensor resistor 27a is outside of the corresponding lower and upper resistance limits and testing proceeds to the second gas sensor. Otherwise, the testing for sensor resistor 27a proceeds to step 42.3 where S1 is tested with upper limit U1. If S1 is greater than or equal to U1, the NO_WIN1 flag for sensor resistor 27a is set, indicating that the sensor resistance for sensor resistor 27a is outside of the corresponding resistance window. If S1 is less than upper limit U1, a flag is set at step 42.7 indicating that the sensor resistance for sensor resistor 27a is inside its resistance window. Following step 42.5 or 42.7, microprocessor 26 proceeds to test the second gas sensor GS2 according to the algorithm in FIG. 12. It will be appreciated that, for the embodiment of the testing algorithm illustrated, testing for the second gas sensor GS2 and the third gas sensor GS3 set forth in FIGS. 12 and 13 should proceed in the same manner as discussed with respect to the testing of the gas sensor GS1 discussed above with reference to FIG. 11.

Figure 12:
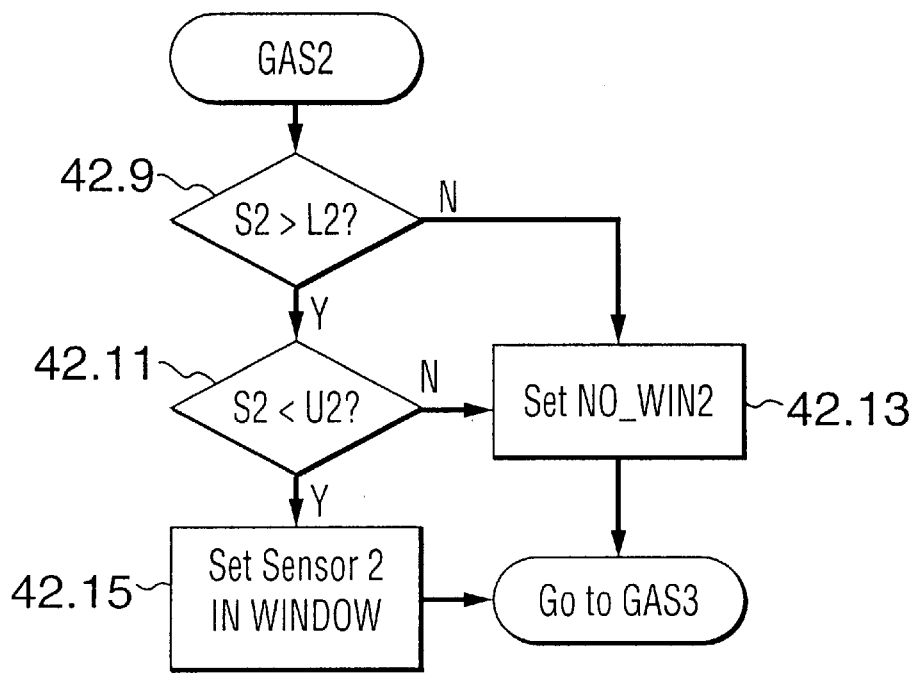
FIG. 12 is a flow chart illustrating one embodiment of the steps for determining if the sensor resistance for sensor resistor 27b of FIG. 5 is within a window of upper and lower limit values in accordance with the present invention.

If one replaces 27a by 27b, 42.1 by 42.9, 42.3 by 42.11, 42.5 by 42.13, 42.7 by 42.15, S1 by S2, L1 by L2, NO_WIN1 by NO_WIN2, SENSOR 1 by SENSOR 2, and GAS2 by GAS3, the above explanation for FIG. 11 applies also to FIG. 12.

Figure 13:
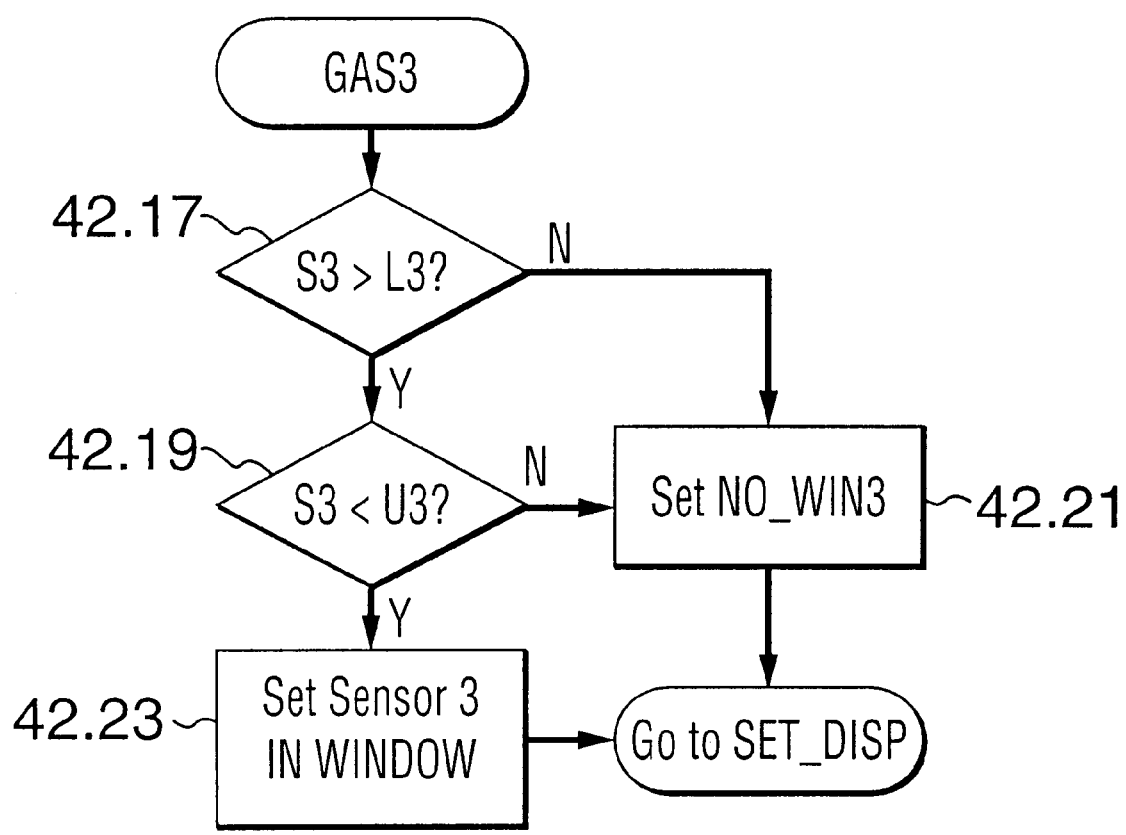
FIG. 13 is a flow chart illustrating one embodiment of the steps for determining if the sensor resistance for sensor resistor 27c of FIG. 5 is within a window of upper and lower limit values in accordance with the present invention.

Similarly, if one replaces 27a by 27c, 42.1 by 42,17, 42.3 by 42.19, 42.5 by 42.21, 42.7 by 42.23, S1 by S3, L1 by L3, NO_WIN1 by NO_WIN3, SENSOR 1 by SENSOR 3 and GAS2 by SET DISP, the above explanation for FIG. 11 applies also to FIG. 13.

Figure 14:
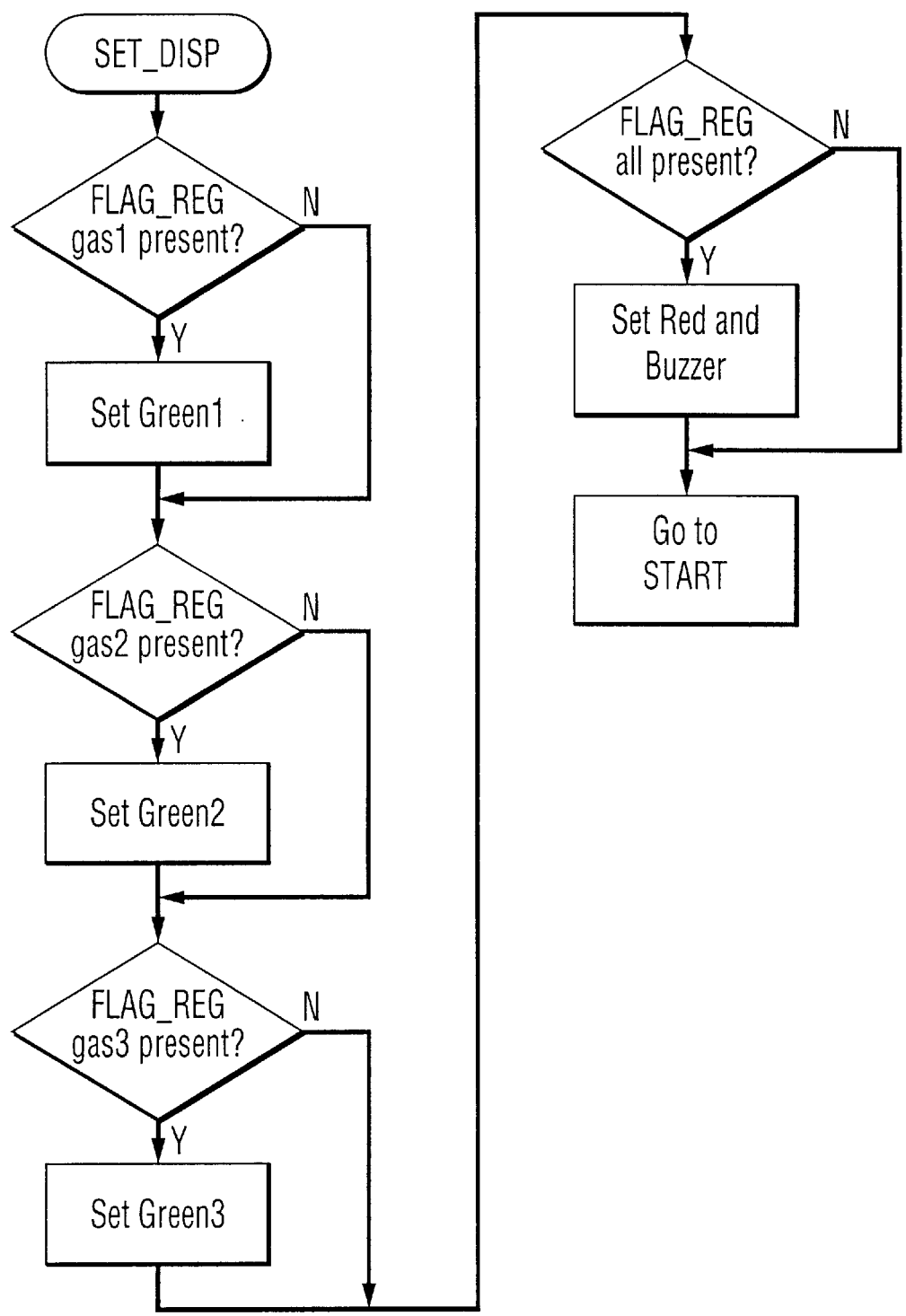
FIG. 14 is a flow chart illustrating one embodiment of the steps for displaying the results of the tests performed in FIG. 11, FIG. 12, and FIG. 13 in accordance with the present invention.

Referring to FIG. 14, once the testing of the third sensor resistor 27c is complete, microprocessor 26 proceeds to display the results using LED1 to LED4 and buzzer 28. As indicated in FIG. 14, for each of sensor resistor 27a, 27b, and 27c found to have a resistance within its corresponding resistance window as tested in FIGS. 11 to 12, a flag (Green1, Green2, and Green3) is set triggering the corresponding LED (LED1, LED2, and LED3). If all three sensor resistors are within their respective resistance windows, a flag for LED4 (Red) is set and buzzer 28 is activated.

Referring to FIG. 15, there is shown an example of one arrangement of commercially available sensor heads which can be used in the present invention to selectively detect hydrogen gas. In this case, three sensor heads available from Figaro Corporation are used: TGS-813, TGS-812, and TGS-822. Each of these gas sensors have a different response to the presence of hydrogen at a predetermined concentration as measured in air. For example, at 500 ppm concentration of hydrogen, the three sensors show sensor resistances of 10.4 kilo Ohms, 1.1 kilo Ohms, and 2.1 kilo Ohms, respectively. These signals are sufficiently electrically far apart from one another to be well suited for the purposes of cross checking discussed earlier.

Referring to FIG. 16, sensor heads TGS-813, TGS-812, and TGS-822 are used in the present invention to detect methane. Each of these gas sensors have a different response to the presence of methane at a predetermined concentration as measured in air. For example, at 500 ppm concentration of methane, the three sensors show sensor resistances of 14.8 kilo Ohms, 37.5 kilo Ohms and 20.8 kilo Ohms, respectively. The signals which can be produced with these sensors are sufficiently electrically far apart from one another to be well suited for the purposes of cross checking in the present invention.

Referring to FIG. 17, sensor heads TGS-813, TGS-812, and TGS-822 are used in the present invention to selectively detect carbon monoxide. Each of these gas sensors has a different response to the presence of carbon monoxide at a predetermined concentration as measured in air. For example, at 500 ppm concentration of carbon monoxide, the three sensors show sensor resistances of 35.8 kilo Ohms, 5.7 kilo Ohms, and 6.1 kilo Ohms, respectively. The signals which can be produced with these sensors are sufficiently electrically far apart from one another to be well suited for the purposes of cross checking in the present invention.

Referring to FIG. 18, sensor heads TGS-813, TGS-812, and TGS-822 are used in the present invention to selectively detect propane. Each of these gas sensors has a different response to the presence of propane at a predetermined concentration as measured in air. For example, at 500 ppm concentration of propane, the three sensors show sensor resistances of 12.7 kilo Ohms, 4.7 kilo Ohms, and 5.6 kilo Ohms, respectively. The signals which can be produced with these sensors are sufficiently electrically far apart from one another to be well suited for the purposes of cross checking in the present invention.

While this invention has been described with reference to illustrative embodiments, this description is not intended to be construed in a limiting sense. Various modifications of the illustrative embodiments, as well as other embodiments of the invention, will be apparent to persons skilled in the art upon reference to this description. For instance, gas sensors with electrolyte mediums rather than resistive mediums may be used wherein upper and lower limits are measured in terms of voltages rather than resistance as with, for example, the selective detection of carbon dioxide. The electrolytes may be liquid or solid. Gas sensors with electrolyte mediums may also be used in combination with gas sensors having resistive mediums. It is therefore contemplated that the appended claims will cover any such modifications or embodiments as fall within the true scope of the invention.

What is claimed is:

1. A gas detection circuit for selectively detecting a predetermined gas, the gas detection circuit comprising:
   (a) a plurality of gas sensors, each gas sensor having a conditioned state different from that of the other gas sensors in the presence of a predetermined gas at a predetermined concentration;
   (b) a sensor measuring circuit coupled to each of said gas sensors and operative to:
      (i) measure the conditioned state of each of said gas sensors; and
      (ii) produce, for each conditioned state measured in (b)(i), an output signal characteristic thereof;
   (c) a cross checking circuit coupled to said sensor measuring circuit and operative to:
      (i) receive each of said output signals corresponding to said respective gas sensors from said sensor measuring circuit;
      (ii) determine, for each of said output signals received in (c)(i), if a corresponding one of said gas sensors has indicated a possible presence of said predetermined gas based on the conditioned state of the corresponding one of said gas sensors; and
      (iii) transmit a detection signal identifying which of said gas sensors has detected a possible presence of said predetermined gas.

2. A gas detection circuit according to claim 1, wherein each of said gas sensors includes a sensor resistor and the conditioned state measured by said sensor measuring circuit in (b)(i) corresponds to a resistance of said sensor resistor.

3. A gas detection circuit according to claim 1, wherein each of said gas sensors includes an electrolyte sensor and the conditioned state measured by said sensor measuring circuit in (b)(i) corresponds to a voltage of said electrolyte sensor.

4. A gas detection circuit according to claim 1, wherein said sensor measuring circuit is operative to:
   (iii) measure an upper limit value and a lower limit value of a responsive characteristic of each of said gas sensors, each pair of said upper and lower limit values defining a window within which the possible presence of said predetermined gas is indicated; and
   (iv) transmit each pair of said upper and lower limit values to said cross checking circuit; and
   wherein said cross checking circuit is operative to determine, in 1(c)(ii), if the conditioned state of the corresponding one of said gas sensors is within the corresponding window of upper and lower limit values.

5. A gas detection circuit according to claim 1, wherein said sensor measuring circuit is operative to:
   (iii) measure an upper limit value and a lower limit value of resistance for each of said gas sensors, each pair of said upper and lower limit values defining a window within which the possible presence of said predetermined gas is indicated; and
   (iv) transmit each pair of said upper and lower limit values to said cross checking circuit; and
   wherein said cross checking circuit is operative to determine, in 1(c)(ii), if the conditioned state of the corresponding one of said gas sensors is within the corresponding window of upper and lower limit values.

6. A gas detection circuit according to claim 5, wherein each of said gas sensors includes a sensor resistor and the conditioned state measured by said sensor measuring circuit in (b)(i) corresponds to a resistance of said sensor resistor.

7. A gas detection circuit according to claim 6, including a pair of limit resistors for each of said gas sensors and wherein the upper and lower limit values of each sensor resistor of said gas sensors measured by said sensor measuring circuit corresponds to a resistance window of each of said gas sensors.

8. A gas detection circuit according to claim 5, including a capacitor and a pair of limit resistors for each of said gas sensors, each pair of resistors coupled to said capacitor and said sensor measuring circuit;
   wherein each of said gas sensors includes a sensor resistor;
   wherein said sensor measuring circuit is operative to:
   (v) charge said capacitor by applying a voltage through ones of said limit resistors and said sensor resistors; and
   (vi) measure, for each of said limit resistors and said sensor resistors, a time required to charge said capacitor through the ones of said limit resistors and said sensor resistors; and
   wherein the conditioned state of each of said gas sensors in 1(b)(i) corresponds to the time required to charge said capacitor through a respective one of said sensor resistors; and
   wherein each pair of said upper and lower limit values of each of said gas sensors corresponds to a pair of times required to charge said capacitor through each of said pair of limit resistors corresponding to one of said gas sensors.

9. A gas detection circuit according to claim 8, wherein each of said gas sensors includes a sensing material in which the electron charge transport is a resistive medium and a heater element so as to maintain the corresponding resistive medium at a temperature above an ambient temperature of air.

10. A gas detection circuit according to claim 9, wherein said plurality of gas sensors is at least three.

11. A gas detection circuit according to claim 9, wherein the predetermined gas is selected from the group consisting of: carbon monoxide, methane, ethanol, propane, isobutane, hydrogen, hydrazine, benzene, and ammonia.

12. A gas detection circuit according to claim 5, wherein each of said gas sensors includes a sensing material in which the electron charge transport is a resistive medium and a heater element so as to maintain the corresponding resistive medium at a temperature above an ambient temperature of air.

13. A method of selectively detecting a predetermined gas with a plurality of gas sensors, each gas sensor having a response different from that of the other gas sensors in the presence of a predetermined gas at a predetermined concentration, the method comprising the steps of:
   measuring a value corresponding to a state of each of said gas sensors;
   determining, for each of said gas sensors, if the value from said measuring step is within a window of upper and lower limit values so as to determine if a possible presence of the predetermined gas is indicated by the corresponding one of said gas sensors; and
   transmitting a signal indicating which of said gas sensors indicates the possible presence of the predetermined gas based upon said determining step.

14. A method according to claim 13, wherein each of said gas sensors includes a sensor resistor and said measuring step includes the step of:
   measuring a resistance of each of said sensor resistors.

15. A method according to claim 14, including, before said determining step, the step of:

measuring a limit resistance of each of a plurality of limit resistors, each limit resistance corresponding to one of said upper and lower limits values.

16. A method according to claim 13, wherein each of said gas sensors includes a sensor resistor, said sensor resistors coupled to a capacitor, said measuring step including the step of:

measuring a time required to charge a capacitor to a predetermined charge by applying a voltage through the sensor resistor of a one of said gas sensors being measured wherein the measured time corresponds to the state of the one of said gas sensors being measured.

17. A method according to claim 13, wherein each of said gas sensors includes a sensor resistor, said sensor resistors coupled to a capacitor, said measuring step including the steps of:

measuring a first charging time required to charge said capacitor to a predetermined charge by applying a first voltage through the sensor resistor of one of said gas sensors being measured wherein the first charging time corresponds to the state of the one of said gas sensors being measured;

measuring a second charging time required to charge said capacitor to the predetermined charge by applying a second voltage through a lower limit resistor corresponding to the one of said gas sensors being measured wherein the second charging time corresponds to a lower limit value of the one of said gas sensors being measured; and measuring a third charging time required to charge said capacitor to the predetermined charge by applying a third voltage through an upper limit resistor corresponding to the one of said gas sensors being measured wherein the third charging time corresponds to an upper limit value of the one of said gas sensors being measured.

18. A method according to claim 17, including the step of:

maintaining a sensor resistive compound in each of said gas sensors above an ambient temperature.

19. A method according to claim 18, wherein said plurality of gas sensors is at least three.

20. A gas detection circuit according to claim 13, wherein the predetermined gas is selected from the group consisting of: carbon dioxide, carbon monoxide, methane, ethanol, propane, isobutane, hydrogen, hydrazine, benzene, and ammonia.

* * * * *